(12) United States Patent
Zhang (10) Patent No.: US 6,528,086 B2
(45) Date of Patent: *Mar. 4, 2003

(54) METHODS AND APPARATUS FOR DRUG DELIVERY INVOLVING PHASE CHANGING FORMULATIONS

(75) Inventor: Jie Zhang, Salt Lake City, UT (US)

(73) Assignee: Zars, Inc., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/407,720

(22) Filed: Sep. 28, 1999

(65) Prior Publication Data
US 2002/0004063 A1 Jan. 10, 2002

(51) Int. Cl.⁷ ............................. A61F 13/00; A61K 9/00; A61K 47/30; A01N 25/34
(52) U.S. Cl. ................ 424/449; 424/400; 424/78.02; 424/443; 424/402; 424/448; 514/772.2; 514/817; 514/944
(58) Field of Search ............................... 424/449, 443, 424/448

(56) References Cited

U.S. PATENT DOCUMENTS 4,695,465 A * 9/1987 Kigasawa et al. .......... 424/445
5,370,879 A * 12/1994 Masterson et al.
5,658,583 A * 8/1997 Zhang et al.
5,733,572 A * 3/1998 Unger et al.
6,036,966 A * 3/2000 Youssefyeh
6,211,250 B1 * 4/2001 Tomlinson et al. ......... 424/449
6,245,347 B1 * 6/2001 Zhang et al. ............... 424/402
6,324,424 B1 * 11/2001 Ledger et al. .............. 424/449

* cited by examiner

Primary Examiner—Thurman K. Page
Assistant Examiner—Isis Ghali
(74) Attorney, Agent, or Firm—Kirton & McConkie; Michael F. Krieger (57) ABSTRACT

This invention relates to an apparatus and method of drug delivery on a human body surface. The formulation comprises a drug, a conversion agent capable of converting the formulation from a less solid phase to a coherent, soft, solid phase, and a vehicle medium or carrier for the drug and conversion agent. The drug formulation is applied to this human body surface in its less than solid phase and is subsequently converted to a soft solid phase while the drug is being delivered through the human body surface. After delivery of the drug is complete, the soft solid formulation can be removed or peeled from the body surface as a coherent solid formulation. The drug formulation provides control over drug delivery rates and allows the formulation to be removed without leaving a messy, residual formulation on the body surface.

85 Claims, 3 Drawing Sheets

METHODS AND APPARATUS FOR DRUG DELIVERY INVOLVING PHASE CHANGING FORMULATIONS

BACKGROUND OF THE INVENTION

1. Field of the Invention

This invention relates to methods, formulations, and apparatus that allow fluid and less-than-solid pharmaceutical formulations to be applied onto certain human body surfaces and then be converted into a more solid state, thereby facilitating administration and removal of the formulation after application.

This invention also relates to methods and formulations that can anesthetize the skin or certain compromised human body surfaces and proximate tissues, such as skin having an abrasion, laceration, or post-surgery wound. More specifically, the present invention relates to less-than-solid anesthetic formulations and delivery systems that can be applied to the skin or compromised surfaces and subsequently converted to a soft coherent solid state and then peeled off the after the anesthetic effect is achieved.

In addition, this invention relates to applying formulations in which most of the local anesthetic agents are applied in an undissolved state onto a human body surface which is substantially lacking a barrier or layer of the skin, such as the stratum corneum, for obtaining more controlled and extended release of the local anesthetic agent(s).

2. Background of the Invention

Many medical formulations topically applied onto human body surfaces are in the form of pastes, gels, ointments, cream, solutions similar less than solid states that are vulnerable to being wiped off inadvertently or flowing away from the application site. For example, after a solution formulation is applied onto human skin, it can flow away quickly and thus result in a short contact time with the original application site. After a cream is applied onto the skin of an arm, it can be rubbed off in the daily activities if not protected by a cover. If a minoxidil cream or solution is applied onto the scalp for promoting hair growth before sleeping, it can be rubbed off on the pillow overnight. In addition, many "less-than-solid" formulations are messy and take an effort to remove.

Topical delivery of anesthesia is a good example of how prior art delivery methods and formulations are limited. Medical procedures on the skin are often painful. Most people are familiar with the pain and discomfort associated with minor procedures on the skin, such as receiving stitches or having a mole removed. Patients undergoing these procedures appreciate the benefits of fast and effective anesthesia. Even recently developed cosmetic procedures, such as laser resurfacing of skin and laser removal of port wine stain or similar birth marks, require significant anesthesia. Cosmetic procedures on facial skin can be especially painful. Currently, several prior art methods may be used to anesthetize the skin before administering these medical and cosmetic procedures, including general anesthesia or regional nerve block by injection, local anesthesia delivered by injection, and local anesthesia delivered topically, such as applying a eutectic mixture of local anesthetic cream (EMLA cream) onto the skin.

Prior art methods for anesthetizing skin have serious drawbacks. General anesthesia or regional nerve block by injection usually requires the involvement of an anesthesiologist and typically cannot be performed in a private practice setting. Injection of local anesthetic is painful, invasive, and may change the shape of the skin surface. It will also leave needle holes in the skin and may scab or scar. The disadvantages of needle injection may be especially unacceptable when the anesthesia is to be delivered to the facial tissues. While the use of EMLA cream is noninvasive, the onset time is often too long. Additionally, EMLA cream needs to be covered with an occlusion membrane while waiting for the anesthetic effect and EMLA cream leaves a mess on the skin which needs to be removed after the anesthetic is delivered.

Just as patients benefit from effective anesthetizing of the skin for certain medical and cosmetic procedures, patients experiencing discomfort as the result of compromised human body surfaces and the procedures associated with treating compromised surfaces can also benefit from convenient local anesthesia. Patients with open wounds, such as abrasions, lacerations, or ulcers may require anesthesia to control pain and to cleanse or close the wound. Chronic ulcer surfaces, surfaces that have scabs and dead tissues (i.e. recovering burn wound), need to be debrided from time to time.

Debridement is a painful procedure if anesthesia is not provided. General analgesia, intravenous narcotic analgesics, regional nerve block by injection, and epidural anesthesia may be used to control the pain associated with debridement or wounds. However, delivery of a general analgesic, regional nerve block by injection, epidural, or intravenous analgesic typically requires specially trained medical personnel and/or special medical equipment to administer. The procedures also expose patients to significant risks and expose care givers to significant liability. Applying analgesic formulation in which most of the active drug is dissolved onto skin lacking stratum corneum may result in dangerously rapid absorption of the drug and short duration of the effect.

Some local anesthetic agents used in the prior art formulations and apparatus of this invention to noninvasively anesthetize or provide analgesia to human body surfaces and tissues under the surface have significant limitations. Some commonly used local anesthetics, such as lidocaine have relatively limited penetration and sustain the analgesic effect for a relatively short period of time.

Thus, it would be advantageous to develop methods in which the formulation is in the less-than solid form, such as a paste, gel, ointment, cream or solution, before being applied onto a human body surface and then the formulation can be converted into a coherent, solidified gel by a certain mechanism during the application to facilitate removal. For some medications, it would also be advantageous if the means for converting the formulation into a coherent solid also included an occlusive cover that inhibited the evaporation of the solvent in the formulation and prevented the formulation from being rubbed off.

It would be particularly advantageous to develop methods and formulations to conveniently and noninvasively anesthetize the skin, especially the facial skin. It would also be advantageous to develop methods and formulations to more conveniently and safely anesthetize compromised human body surfaces. It would further be an advantage to develop an anesthetic formulation that can delivery anesthetic quickly and transdermally and that can be removed easily.

In this application, the phrase "less-than-solid phase," "less-than-solid state," or "less-than-solid form" means, unless specifically described otherwise, a form that is not as hard and as coherent as a solidified gel. Examples of such "less-than-solid" substances include toothpaste, cream, ointment, etc. One common property of these "less-than-solid" substances is that the substance is not strongly cohesive, or in other words, the substance is a liquid or a highly viscous fluid. In practical terms, a "less-than-solid" substance is a substance that one cannot grab and lift as a cohesive whole.

SUMMARY AND OBJECTS OF THE INVENTION

The present invention is directed toward a method and device for dermal delivery of a drug formulation. More specifically, the invention is a method and device for delivering a topically delivered drug using a formulation which is applied to a patient's skin as a fluid, moldable, or less-than-solid drug formulation, but which can be subsequently converted to a coherent, soft solid phase to facilitate removal of the formulation.

The formulation generally comprises a topically delivered drug, a conversion agent, and a vehicle medium or carrier. The drug is dispersed in the carrier. The conversion agent may be included in the drug formulation with the vehicle medium (carrier) and the drug or may be added following the application of the formulation. At the time of application of the formulation to the skin, the formulation is in a less-than-solid phase. At the conclusion of the treatment, the formulation is a coherent, soft solid that can be cleanly peeled from the skin.

The topically delivered drug or pharmaceutical can be a single drug, such as a single local anesthetic, or a combination of drugs, such as a eutectic mixture of lidocaine and tetracaine. The drug may be dispersed throughout the formulation in a solid form, dissolved in oil droplets which are dispersed in the vehicle medium, or in aqueous solution within the vehicle medium. The drug should be capable of transdermal delivery and have a permeability rate which allows controlled and effective delivery of the drug using the present invention. Alternatively, the drug may have a permeability rate which can be enhanced so as to be effective with the present invention, such as with permeation enhancers.

The vehicle medium may be one or more pharmaceutical excipients known in the art. The vehicle medium may also provide a stable environment for the drug. For example, the vehicle medium may contain buffers to maintain an appropriate pH or may contain agents to reduce hydrolytic reactions among the ingredients of the formulation. The vehicle medium also facilitates the application of the formulation. Ingredients which allow the formulation to maintain a desired viscosity during application can make applying the formulation easier. The vehicle medium will also facilitate delivery of the drug. Permeation enhancers can be included in the vehicle medium to increase the absorption rate of the drug. The vehicle medium may also aid in the removal of the formulation after delivery. Specifically, the vehicle medium may contain ingredients such as emulsifying agents, plasticizers, viscosity agents, and hygroscopic agents.

The conversion agent provides the formulation with the ability to change from one phase to another more solid and coherent phase, such as from a liquid or cream to a soft solid. The formulation is applied to a patient's skin in such a way as to form a continuous layer of formulation. (Naturally, the formulation can be applied to different areas of a patient's skin to form several, different "continuous layers.") When the phase change occurs, the solidified formulation is more easily removed from the patient's skin. The formulation does not leave behind residues or films. It is possible that in some circumstances many formulations in the forms of gel, cream, or paste can be dried to yield a solid. However, A unique feature of the formulation in this invention is that the solid phase (which is converted from the original less-than-solid formulation) is coherent and has a certain strength so it can be peeled off the body surface as a layer, leaving little residual formulation. The formulation in solid form will also be flexible and not brittle.

For some formulations, the phase change may be passively triggered. Passive initiation of the phase change can be the result of a change in environment as the formulation is taken out of storage and is applied to the skin of the patient. Passive initiation does not require the patient or caregiver to actively begin the formulation's conversion process; the conversion process is initiated by some naturally occurring condition. For example, a phase change that is passively initiated occurs when the water content of the formulation changes due to evaporation to the atmosphere and the remaining pharmaceutical ingredients may comprise a gelling agent which allows the formulation to convert to a soft, coherent solid or gel. If polyvinyl alcohol is an ingredient in a cream formulation of the present invention, the polyvinyl alcohol can act as a conversion agent and transform the cream formulation into a solid as the formulation loses water to the atmosphere through evaporation. Other potential environmental triggers which can initiate a passive phase change include, but are not limited to, exposing the formulation to human body surface temperature and/or exposing the formulation to air or to light. These passive triggers can also act as a safety mechanism to help prevent over dosing.

Another mechanism for converting a liquid, paste, or cream formulation into a coherent, solidified gel involves the use of thermally reversible gel polymers (a "thermal gel"), such as Pluronic F127 made by BASF Corporation, USA. A solution containing certain amount of thermal gel generally stays as a liquid at room temperature and becomes a non-fluid gel after the temperature is increased to a certain level. Some embodiments of this invention use thermal gel in liquid, paste, or cream pharmaceutical formulations. The formulation stays a viscous liquid, such as paste or cream, at room temperature. When the formulation is applied to human body surface, the body temperature causes the thermal gel to convert the formulation into a non-fluid gel. The non-fluid, "non-flowable" gel has advantages over the original form of the formulation because the non-fluid gel is harder to rub off, do not flow away from the application site and yet can still be removed easily.

In order to achieve the conversion to the non-fluid gel on a human body surface, the conversion temperature may need to be optimized by specially designing the chemical structure and/or components of the thermal gel polymer. For example, thermal gels designed to be used in injectable formulations such as are found in the prior art may have a conversion temperature around 37° C. However, the temperature of a topically applied formulation may only be increased to around 30° C. by the skin. Therefore, in order for the conversion to occur on the skin, the conversion temperature must be around or below 30° C. This may be achieved by changing the structure of the thermal gel polymer.

The conversion agent may additionally or alternatively be actively triggered. The patient or care-giver can activate the conversion agent either by actively changing the ambient environment around the formulation or by altering the chemical makeup of the formulation. The active initiation causes the formulation to change to a more solid phase. For example, solutions containing certain polymers undergo phase changes from liquid to solid form upon exposure to high levels of certain wavelengths of light. The patient or caregiver may actively initiate a phase change in the formulation by exposing a formulation containing such polymers to a high level of light having the appropriate corresponding wavelength. Similarly, the phase change can be actively initiated by adding a pharmaceutical ingredient to the formulation after removal from storage or after it is applied, such as applying a crosslinking agent to a formulation containing a crosslinkable ingredient. Formulations that allow the patient or caregiver to select when to initiate the phase change give additional control and flexibility over the drug delivery process, allowing the user to decide when to convert the formulation to gel (and thereby affect delivery of the drug) or to decide not to convert the formulation, if for some reason doing so is undesirable of unnecessary.

The method of the present invention comprises the first step of removing the formulation from its storage environment. The particular storage environment for each embodiment of the present invention may differ depending upon the nature of the formulation and the drug being used. For instance, a formulation may require a refrigerated storage environment that limits the exposure of the formulation to ambient temperature and/or air. Such an environment may be provided by storing the formulation in an air-tight container within a refrigerated compartment Other formulations may require limited exposure to light prior to administration. Some formulations will not require specialized storage environments.

After removing the formulation from the storage environment, the formulation is applied as a fluid, or other less-than-solid form, to a human body surface. The formulation may be molded or manipulated so that the surface being treated is covered by a substantially even layer of the formulation. A formulation applicator may be used to give the formulation layer a desired thickness. For certain drug formulations of the present invention, controlling the thickness of the formulation layer on the skin provides a measure of control over the delivery of the drug and over the time it takes for the drug formulation to complete its phase transition.

In view of the foregoing, the present invention provides a formulation, apparatus, and method for delivering a drug formulation that can be applied to and then peeled off a patient's body surface after delivery of the drug. The formulation does not need to be rubbed or washed off the body surface. This approach to drug delivery through a patient's body surface is safer because it is non-invasive and time controlled. The present invention can also save time by reducing the time required to clean up after application of the drug formulation.

The formulation and method of the present invention also allow the rate of the drug to be controlled. This can be especially important in applications which involve body surfaces that do not have a "protective barrier" such as a layer of stratum corneum. Dermally delivered drugs which are applied to skin or a body surface which does not have a protective barrier can be rapidly absorbed and cause dangerously high rates of uptake. Furthermore, the drug can be absorbed too quickly so as to prevent the drug from having any extended therapeutic affect.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through the use of the accompanying drawings in which:

DETAILED DESCRIPTION OF THE PREFERRED EMBODIMENT

It will be readily understood that the components of the present invention, as generally described and illustrated in the figures herein, could be arranged and designed in a wide variety of different configurations. Thus, the following more detailed description of the embodiments of the system and method of the present invention, as represented in FIGS. 1 through 7, is not intended to limit the scope of the invention as claimed, but it is merely representative of the presently preferred embodiments of the invention.

The present invention relates to drug formulations and delivery systems that can be applied to and then peeled off the skin and/or off compromised human body surfaces after the drug delivery is achieved. The formulation is altered after removal from its storage container so that it undergoes a phase change from a less solid to a more solid state. Depending on the formulation, this phase change is passively triggered or actively triggered. Another formulation of the present invention is designed so that it is not converted to a solid gel. The present invention is also directed to an drug formulation for delivering a drug at a controlled rate to a body surface lacking a protective barrier that limits absorption (e.g. stratum corneum).

One embodiment of the present invention employs a passively triggered drug formulation (hereinafter the "first formulation" or "Formulation I"). The first formulation is in the form of viscous liquid, cream or paste in that it can be applied as a layer of certain thickness to the skin or compromised body surface where drug delivery will take place. The first formulation layer turns into a coherent, soft and peelable layer as the solvent (i.e. water, alcohol) in the formulation evaporates. Therefore, after the therapeutic effect of the drug is achieved, the "dried" formulation can be peeled off the skin, leaving little residual formulation on the skin.

A second embodiment involves a viscous liquid, cream or paste drug formulation (hereinafter the "second formulation" or "Formulation II") that is actively initiated. This second formulation contains a crosslinkable, but uncrosslinked polymer. The formulation is applied to the skin and then subsequently converted to more solid state by being covered with a solidifying cover. The solidifying cover contains a crosslinking agent capable of converting said formulation into a solid gel. After the drug is delivered and the formulation is converted to the form of solid gel, the formulation can be peeled off the skin, leaving little residual material on the skin.

Formulations in both of the above embodiments may contain local anesthetics in forms suitable for skin penetration and may be used together with ingredients known in the art such as emulsifying agents, thickening agents, and solvents. Both anesthetic embodiments of the two formulations may be used to anesthetize compromised body surfaces, such as broken skin, a wound or ulcer surface, a post surgical wound, and a surface with scabs and dead tissues that needs to be debrided. Alternative applications may require some different properties for each of the formulations, such as sterility or higher viscosity, and may thus require different pharmaceutical ingredients.

Different applications and uses of the present invention may also impose different requirements of the formulation. For example, when used to deliver anesthetic, it is preferable for the embodiment disclosed in the first formulation to be able to numb the skin within a relatively short period of time and to cause relatively little skin irritation.

Formulation I should also be easy to apply and remove, which means it should be in the form of a cream or paste when applied onto the skin, but should form a solid gel so that it can be easily peeled off the skin without leaving a mess on the skin.

Table A shows a preferred range of weight percentages for ingredients in the first formulation. Tables B, C, and D show three examples of anesthetic embodiments of Formulation I which are passively activated.

TABLE A

Formulation I

| Ingredient | Weight Percentage |
|---|---|
| pharmaceutical agent (may be eutectic mixture) | 0.1–40 |
| polyvinyl alcohol | 2–30 |
| glycerol | 2–30 |
| lecithin | 0.2–10.0 |
| Water Lock ® A-100 (or A-180) | 0–6.0 |
| water | 30–95 |

TABLE B

Anesthesia Formulation $I_A$

| Ingredient | Weight Percentage |
|---|---|
| 1:1 (w:w) eutectic mixture of lidocaine and tetracaine | 4.7 |
| polyvinyl alcohol | 9.3 |
| glycerol | 16.0 |
| lecithin | 2.3 |
| Water Lock ®*A-100 | 1.6 |
| water | 66.1 |

TABLE C

Anesthetic Formulation $I_B$

| Ingredient | Weight Percentage |
|---|---|
| 1:1 (w:w) eutectic mixture of lidocaine and tetracaine | 12.0 |
| polyvinyl alcohol | 8.4 |

TABLE C-continued

Anesthetic Formulation $I_B$

| Ingredient | Weight Percentage |
|---|---|
| glycerol | 16.0 |
| lecithin | 2.3 |
| Water Lock ®*A-100 | 1.6 |
| water | 59.7 |

TABLE D

Anesthetic Formulation $I_C$

| Ingredient | Weight Percentage |
|---|---|
| 1:1 (w:w) eutectic mixture of lidocaine and tetracaine | 4.7 |
| polyvinyl alcohol | 8.3 |
| glycerol | 24.0 |
| lecithin | 2.3 |
| Water Lock ®*A-100 | 1.6 |
| water | 59.1 |

TABLE E

Anesthetic Formulation $I_D$

| Ingredient | Weight Percentage |
|---|---|
| 1:1 (w:w) eutectic mixture of lidocaine and tetracaine | 14.0 |
| polyvinyl alcohol | 8.5 |
| glycerol | 14.0 |
| lecithin | 2.1 |
| Water Lock ® A-180 | 1.5 |
| water | 59.9 |

Water Lock® is a series of water absorbent polymers made by Grain Processing Corporation, Iowa, USA. The A-100 series of Water Lock® is classified as Starch Graft poly (2-propenamide-co-2-propenoic acid, sodium salt). The assigned INCI nomenclature for the A-100 series is Corn Starch, Acrylamide/Sodium Acrylate Copolymer. The G-400 is classified as Graft poly(2-propenamide-co-2-propenoic acid, sodium salt) with a INCI nomenclature of Acrylamide/Sodium Acrylate Copolymer. The G-400 is more water absorbent than A-100 series, and therefore may be used in smaller quantities.

In Formulations $I_A$, $I_B$, $I_C$, and $I_D$, the eutectic mixture of lidocaine and tetracaine, in the form of oil droplets emulsified in the formulation, are the active anesthetic ingredients. Polyvinyl alcohol is the polymer that can convert the cream into a solid after enough of the water in the formulation is evaporated. Glycerol serves as a plasticizing agent, which allows the formulation to become a soft, flexible solid, rather than a rigid one, after the evaporation of the water. Glycerol also has a tendency to retain water. Lecithin is the emulsifying agent that keeps the eutectic mixture in the form of tiny oil droplets in the formulation.

Water Lock® is used to retain water as well as to increase the viscosity, so that the formulation has a minimal ability to flow. The control of water loss and retention is an important part of the present invention and is particularly important in embodiments such as Formulations $I_A$, $I_B$, $I_C$, and $I_D$. The inventor believes that in the formulations, only the drug molecules that are dissolved in the water of the formulation can effectively penetrate the skin. Therefore, a key, novel feature of the formulation is the ability to control the balance between water retention and water loss.

Water in the formulation is retained long enough to allow sufficient amounts of the drug to be delivered into the skin within a reasonable time, while at the same time permitting enough water to be lost by evaporation so that the formulation becomes a soft solid that can be easily peeled off the skin after the numbing effect is achieved. More specifically, if the water is lost too fast, the formulation will prematurely stop delivering the drug at sufficient rates so that the skin will not be anesthetized as intended. If the water is lost too slowly, portions of the formulation will remain in a less-than-solid state even after the skin is anesthetized and it is generally more difficult to remove a less-than-solid formulation than a solidified formulation.

In this formulation, the water retaining ability of the formulation is provided by Water Lock® and glycerol. Water Lock® also contributes to the viscosity of the formulation on the skin. Thickness of the formulation on the skin is an important factor of the present invention and especially the embodiments similar to Formulation I. If the layer of formulation on the skin is too thin, the formulation will dry out before sufficient amounts of the drug are delivered. If the layer is too thick, the portion in contact with the skin will remain as a cream, while the outside layer exposed to air may solidify. The thickness of the layer should be adjusted to correspond with the appropriate water loss and water retention requirements of a given formulation and given therapeutic need. For example a thicker layer of the formulation should be used to achieve anesthesia with greater depth. That is because the formulation in contact with the skin can retain water for a longer period of time, and hence deliver the drug for longer time, if the layer is thicker.

For the first formulation containing local anesthetic, the optimal thickness should be somewhere between 0.5–3 mm, more likely between 1–2 mm, depending on the length of time it takes to anesthetize the particular skin, and how dry the ambient air is. Therefore, it is another novel approach of this invention to control the timing of the drying of the formulation by selecting optimal thickness of the formulation on the skin or other body surfaces. For some applications, employing appropriate devices for conveniently obtaining the desired thickness of formulation on other body surfaces is an important part of this invention.

One of the advantages of the present invention is that it obviates the need to remove the cream from the skin by extensive washing or cleansing of the skin. Washing and cleansing the skin takes extra effort and time. It can also irritate the skin and compromised body surfaces of the skin. Controlling water retention according to the present invention obviates the need for time consuming clean-up of the drug formulation, while permitting adequate delivery of the drug.

To deliver a drug using the first formulation, the drug formulation is applied to the skin at a desired delivery location. The drug formulation is applied in a layer having a substantially consistent thickness. For drug formulation that use water as a vehicle for skin permeation, the drug continues to be delivered as water evaporates until most of the water the is evaporated and the formulation is a soft peelable solid. For example, to numb the facial skin using the first formulation of the present invention, the formulation can be applied so that the facial skin area to be anesthetized is completely covered by about 1 mm of the formulation. The skin area is usually numbed in 15 to 45 minutes, depending on the individual and location of the skin. Meanwhile, as water in the formulation evaporates, the formulation dries into a layer of soft solid. When the desired anesthetic effect is achieved, the solid gel is peeled off the skin area, leaving virtually no residual mess on the skin. The skin area is anesthetized and if desired can be subjected to a medical treatment or procedure. For drugs that can penetrate the skin without having to dissolve in water first, drug delivery can continue after the water is evaporated.

In the above and similar formulations using eutectic mixtures of drugs in the formulation, the drugs or pharmaceutical agents exist as oil droplets of the eutectic mixture while a small portion of them exist as dissolved molecules in the aqueous phase. The concentrations of pharmaceutical agents in the aqueous phase can be limited by their aqueous solubility and may be quite low depending on the formulation pH and the pKa's of the pharmaceutical agents. For some embodiments of the present invention, drug delivery may be mainly caused by the delivery of pharmaceutical agents dissolved in aqueous phase, rather than by delivery from drug molecules in the eutectic mixture droplets. This means water is necessary to deliver the pharmaceutical agents into the skin for these embodiments.

For formulation embodiments where drug delivery is mainly caused by the local anesthetic agents dissolved in aqueous phase, the control of water content, water retention, and water loss is especially critical. After such a formulation is applied onto the skin. The formulation starts to lose water due to evaporation. For the formulation to work, adequate amounts of the drug must be delivered before so much water is lost that the formulation is unable to deliver the drug at sufficient rates. Therefore, if the formulation is not designed to be covered by a barrier film after being applied on the skin, such as with EMLA cream, the water in the formulation must last long enough to deliver the drug in spite of ongoing water loss. It is, nevertheless still preferable that enough water be evaporated approximately when an adequate amount of the drug will have been delivered, so that the formulation is a layer of peelable, solid that is easy to remove.

Control of water content, water retention and water loss is a unique requirement of the formulations of the present invention that must be addressed in the formulation design and method of use. Therefore it is a unique feature of the formulations and methods in this invention that water is retained long enough to deliver the drug while not so long as to prevent the formulation from becoming a peelable, soft solid in time for easy removal. The appropriate water retention can be achieved by adding water-retaining substances to the formulation and by applying a layer of formulation with certain thickness onto the skin or body surface.

The type of body surface or skin on which the formulation is applied can affect the delivery of the drug. For example, the facial skin is significantly different from skin in other parts of the body. The facial skin is thinner than other areas of skin and has more lipid content. Furthermore, the tissues under the facial skin are generally more vascularized and more innervated than other areas of skin. A formulation applied to the facial skin can have a shorter onset time than the same formulation applied on other areas of skin.

The differences in skin types are important in dermal drug delivery and must be accounted for in designing a formulation for anesthetizing facial skin. For example, because the onset time is shorter on facial skin, it is possible that a given anesthetic formulation would be able to anesthetize the facial skin, but would not be able to anesthetize other skin surfaces. The water loss of the particular formulation may occur too quickly for the formulation to be used to anesthetize some area of skin, whereas the same formulation may work very well on facial skin, because of the shorter onset time for facial skin. The use of certain substances in the formulations may make the formulations have slower onset but may make the formulation more desirable in other ways. High concentrations of glycerol in the formulation may delay the onset time somewhat, but glycerol can make an otherwise hardened formulation soft, can help retain water, and may also make ester type local anesthetic agents more stable in the formulation. Therefore, a formulation containing relatively high concentrations of glycerol may work adequately for anesthetizing the facial skin, but not other areas of skin.

Many drugs and classes of drugs may benefit from the approaches of the present invention, as exemplified in the formulations presented herein. For example, the pharmaceutical agent or drug may be: Antivirals (e.g. acyclovir); Antibiotics (e.g. bacitracin, chloramphenicol, clindamycin, erythromycin, gentamicin, mupirocin, neomycin, tetracylcines); Antifungals (e.g. amphotericin B, benzoic acid, salicylic acid, butaconazole, ciclopirox, clioquinol, clotrimazole, econazole nitrate, haloprogin, ketoconazole, micronazole, naftifine, nystatin, oxiconazole, sodium thiosulfate, terconazole, triacetin, undecyclenic acid, and undecylenate salts); Other Antiseptics (e.g. benzalkonium chloride, hexachlorophene, iodine, mafenide, metronidazole, nitrofurazone, selenium sulfide, silver sulfadiazine); Anti-inflammatory Agents (e.g. corticosteroids); Antipruritics; Cell stimulants and proliferants (e.g. tretinoin for treating acne); Emollients (e.g. vitamins A, D); Agents for Treating Necrotic Tissues and Dermal Ulcers or Used in Debridement (e.g. collagenase, fibrinolysin, deoxyribonuclease, sutilains); Anti-Skin Cancer/Anti-Keratosis Agents (e.g. fluorouracil); Wound Cleansing Agents (e.g. dextranomer); Agents for Promoting Hair Growth (e.g. minoxidil); Depigmenting Agents (e.g. hydroquinone, monobenzone); Sunscreen Agents and Chemical Sunscreen Agents (e.g. aminobenzoic acid derivatives such as aminobenzoic acid and menthyl anthranilate; benzophenone derivatives such as dioxybenzone and oxybenzone; salicylate derivatives; cinnamic acid derivatives; gigalloyl trioleate) and Opaque Physical Sunscreen Agents (e.g. red petrolatum, titanium dioxide, zinc oxide); Other Dermatological and Pharmaceutical Agents such as psoriasis drugs (e.g. anthralin, calcipotriene), drugs for promoting wound healing, drugs for treating warts and moles, drugs for treating ulcerated skin surfaces, drugs used on newborn babies that need to be delivered in a patch form (the adhesive in patches may be too aggressive for newborn babies' skin); drugs that are applied to mucosa (e.g. alprostadil and other drugs for treating male erectile dysfunction (on penis tip and/or into urethra)), drugs for treating mucosal warts (e.g. imiquimod) and drugs for treating insect bites and minor cuts (e.g. local anesthetics ).

For embodiments using a local anesthetic, the drug may be a eutectic mixture of lidocaine and prilocaine or a compound, a mixture, or a eutectic mixture of compounds in the group of lidocaine, tetracaine, prilocaine, benzocaine, procaine, bupivacaine, butacaine, dibucaine, etidocaine, mepivacaine, cyclomethycaine, hexylcaine, and proparacaine.

Many inactive ingredients in the formulation may be substituted without compromising the function of the formulation. Certain substitution of ingredients may even make the formulation more desirable, such as making it more stable, less costly, and/or easier to use or to make. Lecithin is disclosed as a preferred emulsifier, but other compounds such as gelatin, sorbitan esters, polysorbates, poly oxyethylene, fatty acid esters, Pemulen TR1, TR2 (BFGoodrich) may also be used as emulsifying agents. Plasticizing agents other than glycerol may be employed. Certain compounds that have melting points below 30° C., and are water-soluble but much less volatile than water may also be used as plasticizer. These compounds include low molecular weight (i.e. m.w.=600) poly ethylene glycol, and N-methyl-pyrrolidone. Certain oils, such as castor oil, may also serve as plasticizers.

Compounds other than Water Lock® may also be used to provide viscosity and retain water. Compounds that can increase viscosity include polyacrylic polymers, gellan gum, carrageenan, cellulose derivatives such as sodium carboxymethyl cellulose, hydroxyethyl cellulose, hydroxypropyl cellulose. Substances that are hygroscopic or can hold water, such as sorbitol, cotton fibers, and some of the viscosity increasing compounds above may be used to retain water. It is understood that all of the substitute and alternative ingredients and agents disclosed above and below are not exclusive or limiting, but are offered as examples of alternative embodiments of the present invention.

Formulation II is an embodiment of the present invention which contains a crosslinkable but uncrosslinked polymer that can be crosslinked before removal from skin. There are two preferred ways to initiate the crosslinking process. One is to bring the formulation into contact with the cross-linking agent, such as by covering the formulation with a layer of material impregnated with the crosslinking agent. While the formulation begins to deliver the drug, the crosslinking agent diffuses into the formulation and converts the formulation into a solid. Alternatively, Formulation II may include a polymer that can be crosslinked when treated by an outside triggering mechanism such as light with certain wavelengths, such as ultraviolet light. The formulation is converted into a solid gel by such a triggering mechanism after it is applied onto the skin and subjected to necessary levels of ultra violet light. In both cases the formulation forms a solid gel before or around the time when adequate drug delivery is achieved, and thus can be easily peeled off the skin without leaving a mess on the skin.

Table F shows an example of a eutectic mixture drug formulation containing an uncrosslinked but crosslinkable polymer and a range of preferred weight ratios:

TABLE F

Formulation II

| Ingredient | Weight Percentage |
|---|---|
| pharmaceutical agent (may be eutectic mixture) | 0.1–40 |
| polyvinyl alcohol | 2–30 |
| lecithin | 0.5–10.0 |
| Water Lock ® A-100 (or A-180) | 0–6.0 |
| water | 30–95 |

TABLE G

Anesthetic Formulation II$_A$

| Ingredient | Weight Percentage |
|---|---|
| 1:1 (w:w) eutectic mixture of lidocaine and tetracaine | 14.0 |

TABLE G-continued

Anesthetic Formulation II$_A$

| Ingredient | Weight Percentage |
|---|---|
| polyvinyl alcohol | 12.0 |
| lecithin | 2.7 |
| Water Lock ® A-180 | 1.6 |
| water | 66.1 |

In this embodiment, polyvinyl alcohol is the crosslinkable but uncrosslinked polymer. Sodium borate is the crosslinking agent for polyvinyl alcohol, and is impregnated into a layer of gauze. To inhibit the loss of water in the formulation, it is desirable that the gauze is laminated with a layer of flexible plastic material, such as polyurethane film or tape. Other cross linking agents are possible, such as boric acid and salts of boric acid, or other compounds containing boron.

To use the anesthetic embodiment of Formulation II$_A$ as shown in Table G above, the formulation is applied onto the skin area to be anesthetized so that the skin is covered with 0.5–1 mm of the formulation. The borate soaked gauze/plastic film laminate is placed onto the formulation layer, so that the borate soaked gauze is in direct contact with the formulation. The borate gauze contains about 1 mg sodium borate per square centimeter of gauze. Sodium borate in the gauze then diffuses into the formulation to convert it into a coherent, soft solid in about 15–20 minutes by crosslinking the polyvinyl alcohol molecules in the formulation.

Using the anesthetic embodiment of Formulation II$_A$, the skin is numbed in about 30–45 minutes. After the desired anesthetic effect is achieved, the gauze laminate is peeled off the skin. Since the solidified formulation is attached to the gauze layer, it is peeled off the skin with the gauze, leaving no mess on the skin. Of course, the crosslinking agent may be delivered into the formulation by other methods, such as spraying.

Delivery of drugs (other than topically applied local anesthetics) and classes of drugs may benefit from the approach present invention, as it relates to Formulation II and embodiments that are actively initiated. Those drugs include but are not limited to: Antivirals (e.g. acyclovir); Antibiotics (e.g. bacitracin, chloramphenicol, clindamycin, erythromycin, gentamicin, mupirocin, neomycin, tetracylcines); Antifungals (e.g, amphotericin B, benzoic acid, salicylic acid, butaconazole, ciclopirox, clioquinol, clotrimazole, econazole nitrate, haloprogin, ketoconazole, micronazole, naftifine, nystatin, oxiconazole, sodium thiosulfate, terconazole, triacetin, undecyclenic acid, and undecylenate salts); Other Antiseptics (e.g. benzalkonium chloride, hexachlorophene, iodine, mafenide, metronidazole, nitrofurazone, selenium sulfide, silver sulfadiazine); Anti-inflammatory Agents (e.g. corticosteroids); Antipruritics; Cell stimulants and proliferants (e.g. tretinoin for treating acne); Emollients (e.g. vitamins A, D); Agents for Treating Necrotic Tissues and Dermal Ulcers or Used in Debridement (e.g. collagenase, fibrinolysin, desoxyribonuclease, sutilains); Anti-Skin Cancer/Anti-Keratosis Agents (e.g. fluorouracil; Wound Cleansing Agents (e.g. dextranomer); Agents for Promoting Hair Growth (e.g. minoxidil); Depigmenting Agents (e.g. hydroquinone, monobenzone); Sunscreen Agents and Chemical Sunscreen Agents (e.g. aminobenzoic acid derivatives such as aminobenzoic acid and menthyl anthranilate; benzophenone derivatives such as dioxybenzone and oxybenzone; salicylate derivatives; cinnamic acid derivatives; gigalloyl trioleate) and Opaque Physical Sunscreen Agents (e.g. red petrolatum, titanium dioxide, zinc oxide); Other Dermatological and Pharmaceutical Agents such as psoriasis drugs (e.g. anthralin, calcipotriene), drugs for promoting wound healing, drugs for treating warts and moles, drugs for treating ulcerated skin surfaces, drugs used on newborn babies that need to be delivered in a patch form (the adhesive in patches may be too aggressive for newborn babies' skin); drugs that are applied to mucosa (e.g. alprostadil and other drugs for treating male erectile dysfunction (on penis tip and/or into urethra)), drugs for treating mucosal warts (e.g. imiquimod) and drugs for treating insect bites or minor cuts (e.g. local anesthetics).

Tetracaine is a good choice for the local anesthetic agents in the anesthetic embodiments of Formulations I and II. Since tetracaine is subject to hydrolytic degradation in aqueous formulations, it may be desirable to add compounds that can inhibit the hydrolytic degradation. Sufficiently high concentrations of glycerol in the formulation may act as such an inhibiting substance by limiting water-tetracaine contact, which is necessary for hydrolytic reaction to take place in the glycerol-water mixture. Other compounds that may provide similar hydrolysis-inhibiting effect include potyethylene glycol, and N-methyl pyrrolidone. The same method may be used to protect other ester type local anesthetic agents, such as benzocaine, procaine, butacaide, cyclomethycaine, hexylcaine and proparacaine, if they are used in the formulation. Ester type local anesthetics are subject to hydrolytic degradation.

In both of the above embodiments, many local anesthetic agents or combinations of them may be used. However, the use of tetracaine, either in combination with another local anesthetic agent or alone, provides special advantages. Tetracaine, in its unionized form, which are the dominant form in formulations and methods in this invention, can penetrate the skin much faster and deeper than other commonly used local anesthetic agents, such as lidocaine and prilocaine. This feature is especially important to formulations and methods that rely on evaporation of the solvent for conversion to solid. In order for the treatment to be effective, a sufficient amount of the drug must have penetrated the skin before too much solvent (which is necessary to deliver the drug) is evaporated. Thus, the use of tetracaine, especially unionized tetracaine, in formulations that rely on evaporation of solvent for solidifying provides unique advantages for anesthetic delivery.

Tetracaine has also been observed to have a longer lasting anesthetic effect on tissues than lidocaine. Recent research suggests that transdermally delivered tetracaine will have a long-lasting anesthetic effect, even longer than injected lidocaine . Tetracaine, when properly and safely administered is a surprisingly advantageous choice for transdermally delivered local anesthetics.

In addition to drugs that target topical tissues, some drugs that target systemic circulation and regional tissues may also benefit from the approaches in this invention. Those drugs include hormones (e.g. estradiol, testosterone), smoke cessation aid (e.g. nicotine), cardiovascular agents (e.g. nitroglycerin), analgesics (narcotic agents, steroids), anti-inflammatory agents. Many of these agents are currently delivered with transdermal patches that are manufactured with the drug formulation contained in the patch (hereafter "manufactured drug formulation patches"). However, manufacturing the patch to include the drug formulation and subsequent packaging of each individual patch significantly increases the cost of the patch. In addition, altering or modifying the manufactured drug formulation patch during or after the manufacturing process in order to meet a particular therapeutic need can be difficult. For example, the contact area of the manufactured drug formulation patch, which is proportional to the amount of drug delivered, can not be easily varied.

Using the methods and formulations in this invention could significantly reduce the cost and allows the user to easily select the size of the contact area that delivers the amount of the drug that is most suitable to his/her individual need. For example, instead of using manufactured nicotine patches that have a predefined size for smoke cessation, a smoker may squeeze a formulation comprising nicotine and polyvinyl alcohol into an empty patch, (i.e. a foam tape pad with a shallow cavity). The bottom of the shallow cavity is covered with a layer of material impregnated with sodium borate. The foam tapes with desired shallow cavity area may be chosen from many different sizes provided. The foam tape pad with the filled cavity then is applied to user's skin to deliver the nicotine formulation. The selection of the right cavity area allows the user to choose the right delivery dose. After application, the formulation is converted to a coherent solid, in about 20 min, which facilitates easy removal. The foam tape patches can be formed of various sizes and shapes appropriate for the particular treatment. Thus, the drugs and various patches can be manufactured and stored separately and then properly filled and applied before use, making the manufacture of the solid, coherent patch less expensive than manufactured drug formulation patches.

Figure 5:
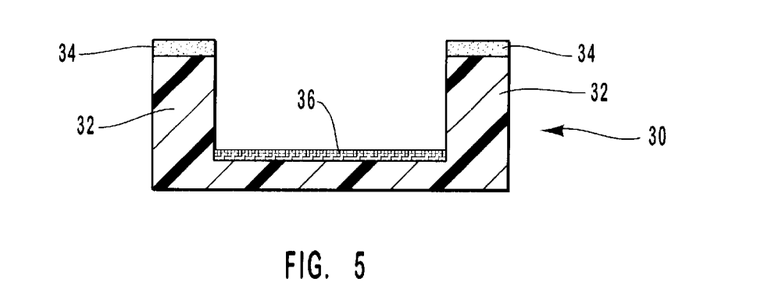
FIG. 5 shows a cross-section of a delivery patch with cross-linking agent.
Figure 6:
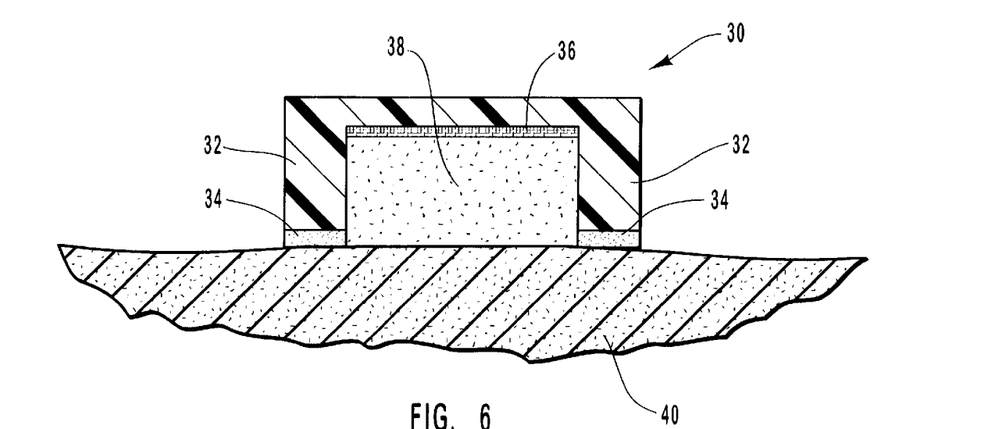
FIG. 6 shows a cross section of a delivery patch with a drug formulation added and disposed on a body surface.
Figure 7:
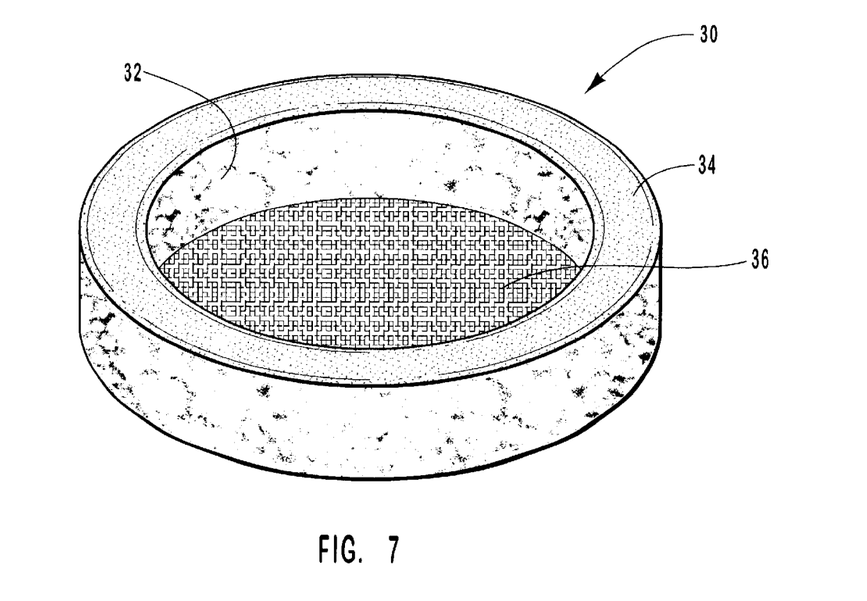
FIG. 7 shows a perspective view of the delivery patch.

Another embodiment of this invention provides a patch with a pre-formed shallow cavity shown in FIGS. 5, 6, and 7, and a formulation comprising a drug and a crosslinkable but uncrosslinked polymer. At the bottom of the cavity is a layer of material impregnated with a crosslinking agent capable of crosslinking the polymer. To use the patch, the user fills the cavity with the formulation and apply the filled patch onto the body surface to deliver the drug. The patch is held to the skin by the adhesive on the patch. After a period of time (e.g. 20 min), the formulation is converted into a solid gel. After the desired application, the patch is removed from the skin. The gelled formulation does not leave a mess on the skin. This method also provides a well defined delivery area, as defined by the area of the shallow cavity.

In both of the above embodiments of the present invention, it is possible in many instances to shorten the onset time of the drug's effect by heating the formulations and the skin under the formulation. Forced air heating, for example, can be used to shorten the onset time of anesthetic effect in the facial skin simply by blowing warm air onto the facial skin. Other heat sources, such as heat lamps or exothermic heating patches, may similarly be used to heat the formulation and the skin, reducing onset time and improving drug delivery. External heating may also be used to contract the solidifying of the gel (e.g. as with formulations which rely on evaporation to solidify the process or with thermal gels) and thus, the rate and the amount. To maintain a homogenous delivery rate, care should be take to evenly heat the formulation on the skin.

One of the applications of the methods and formulations in this invention is to treat insect bites, stings, and minor cuts. Formulations that contain local anesthetic agent and/or other medicine may reduce the pain, itch, or other discomfort caused by insect bites, stings, or minor cuts. A formulation that can be solidified after the application is harder to be rubbed off and easier to remove. The said formulation also forms a protective barrier which may be soothing and may prevent unintentional or undesirable contact with the wound, such as when the patient feels the urge to scratch the insect bite.

The formulations and methods above, with some modifications, can provide unique advantages over prior art local anesthetics in anesthetizing certain compromised human body surfaces For example, if a prior art anesthetic solution in which all or most of the drug is dissolved is applied on to a compromised body surface without skin, most of the local anesthetic agent will be absorbed by the tissues in a relatively short time. That is especially the case where the compromised area does not have its usual barrier to permeation, the stratum corneum. The rapid uptake may fail to provide anesthesia for a sufficient duration in many situations, and more importantly, may also risk producing dangerously high concentrations of the local anesthetic in the patient's blood. Similarly, if a non-coherent gelly formulation (similar to a paste), such as 2% lidocaine hydrochloride gel manufactured by Astra [Xylacaine 2% jelly], is applied, it will be difficult to remove. Attempts to remove such a formulation many further damage the compromised tissues. In addition to being in eutectic mixture and solid particles, the active drug can also exist in oil droplets that are emulsified in the formulation. Table H shows a formulation in which the active anesthetic, tetracaine base is dissolved in oil droplets which are emulsified in the formulation.

TABLE H

Tetracaine Base Dissolved in Oil Droplets Formulation

| Ingredient | Weight Percentage |
| --- | --- |
| Tetracaine base | 5 |
| Castor oil | 15 |
| polyvinyl alcohol | 9.4 |
| lecithin | 2.4 |
| WaterLock ® A-180 | 1.5 |
| Water | 66.7 |

In this kind of formulation, the active drug is dissolved in an oil (i.e. castor oil, oleyl alcohol). The drug-containing oil is emulsified as small oil droplets in the aqueous phase of the formulation, with the help of emulsifying agent(s). The advantage of emulsifying the drug in the oil is that the drug is more evenly distributed in the formulation than it would be using a drug in particle form. Moreover, if the drug is subject to hydrolytic degradation, the oil can provide a "hiding place" or micro-environment to protect the drug from water, and thus reduce the hydrolytic degradation rate. In Formulation I and II, the eutectic mixture of lidocaine and tetracaine provides such an environment or "hiding place" for tetracaine. However, for drugs that cannot form a eutectic mixture with another active drug, this method is a good alternative.

Tetracaine base was first dissolved on castor oil, in a 1:3 weight ratio, to form the oil phase. Polyvinyl alcohol was dispersed in water at about 90° C. before lecithin was added to form the aqueous phase. Water Lock® A180 was added before the oil and aqueous phases were thoroughly mixed to obtain a paste. Applying a layer (1–2 mm) of this formulation onto human arm skin and covering it a foam tape laminated with a layer of gauze impregnated with sodium borate numbed the skin after about 1 hour.

The formulations and methods in this invention provide unique advantages in treating compromised tissues including controlled release of the drug in the formulation and easy removal. For example, in a gelled local anesthetic formulation in which the solubility of the local anesthetic agent is low, and thus most of the local anesthetic agent exists in undissolved form, (i.e. eutectic mixture oil droplets, solid particles, drug dissolved in certain oil droplets), the undissolved anesthetic cannot move nearly as freely nor as fast within the formulation as can the dissolved molecules. That is because the movement of the oil droplets and particles are limited by the polymer gelling agent. Therefore, when such a formulation is brought into direct contact with a wound surface (e.g. an area with compromised outer dermal layer), only the dissolved local anesthetic molecules can move into the tissue by diffusion. (The oil droplets in the formulation that are in direct contact with the skin surface may be absorbed directly into the tissue, but this absorption cannot be sustained. The concentration of local anesthetic molecules dissolved in the aqueous phase of the formulation is limited by solubility and is constant. As dissolved local anesthetic molecules leave the formulation, more local anesthetic molecules will leave the eutectic mixture or particles or oil Droplets and be dissolved into the aqueous solution. As a result, the release rate from the formulation is relatively constant over time, until most of the local anesthetic agent is depleted from the formulation. This avoids "dumping" all the local anesthetic agent into the body in a short time, even when the body surface has minimal barrier to the local anesthetic molecules.

One important application of the local anesthetic formulations discussed above is to provide pain-control for post-surgical wounds. It is believed that providing local anesthetic to the surgical wound may significantly reduce the pain and thus reduce or even eliminate the need for systemic analgesia. Since a surgical wound has no skin protection, the controlled release feature in the formulations in this invention becomes particularly important both in terms of safety against over dose and sufficiently long duration of effect. Thus, it is an important part of this invention to apply a local anesthetic formulation, in which most of the active drug is in undissolved form, to post-surgical wound. The formulation may be in less-than-solid forms such as liquid, viscous liquid, paste, cream; or may be solid gel, and may be incorporated into a patch. For most embodiments, it is desirable that the formulation is converted into a coherent solid to facilitate removal, however, in some embodiments the formulation is left in a less-than-solid form.

It is generally desirable that when the appropriate amount of drug is delivered, the formulation can be removed thoroughly and conveniently. This may be especially important near compromised skin surfaces, where active cleansing to remove the formulation could cause further trauma. The drug formulation in this invention is converted to a coherent and soft solid when the drug delivery is achieved. This makes the removal of the formulation significantly easier than prior art formulations. The drug formulation can be removed at various stages of solidification depending upon the treatment and desired result. For example, a formulation may be removed before the phase change is one hundred percent complete. Generally the formulation will be removed after at least fifty percent of the formulation is converted to a solid.

In some uses, the soft-solid gel itself increases the benefits of the treatment. The gel may provide a measure of protection to skin needing covering. This may be especially advantageous in delivering drugs to compromised skin areas. The soft-solid may help soften or hydrate the skin to facilitate drug delivery or any subsequent treatment. For example, in anesthetizing compromised body surfaces before debridement, it is also desirable that the dead tissues and scabs be softened by hydration. In this regard, the embodiment of the present invention that includes covering the layer of local anesthetic formulation with a solidifying sheet is particularly advantageous. The formulation of the present invention has high concentrations of water. By using the embodiment in which the formulation is covered by a laminated sheet that has a water barrier layer, dead tissues and scabs can be simultaneously treated with a highly hydrated formulation and with an anesthetic.

Compared with formulations for anesthetizing intact skin, a formulation for debridement may need to be relatively fluid, so that it can have good contact with surfaces that are not smooth or have scabs. A formulation having a lower concentration of thickening agent in the formulation can provide a more fluid embodiment.

For reasons discussed above, the thickness of the formulation layer plays an important role in determining when a formulation becomes a solidified and coherent gel, as well whether adequate amounts of drug can be delivered before the formulation dries out and stops delivering due to water evaporation. Thus, it is desirable to have an applicator that allows the caregiver to conveniently apply a layer of formulation with a substantially uniform and predetermined thickness onto the skin.

Figure 1:
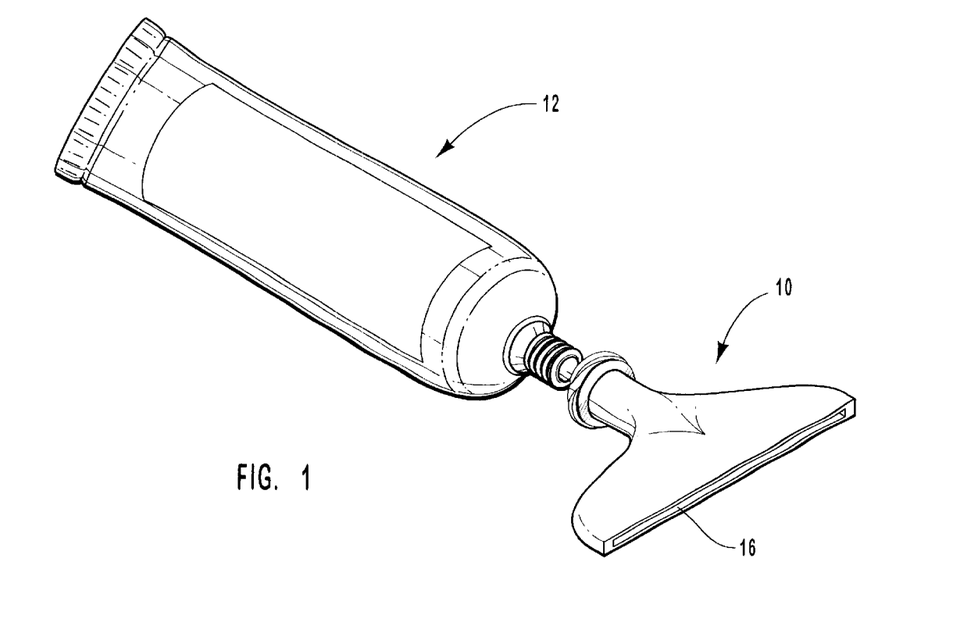
FIG. 1 shows a perspective view of a formulation storage container/delivery tube, with applicator nozzle.
Figure 2:
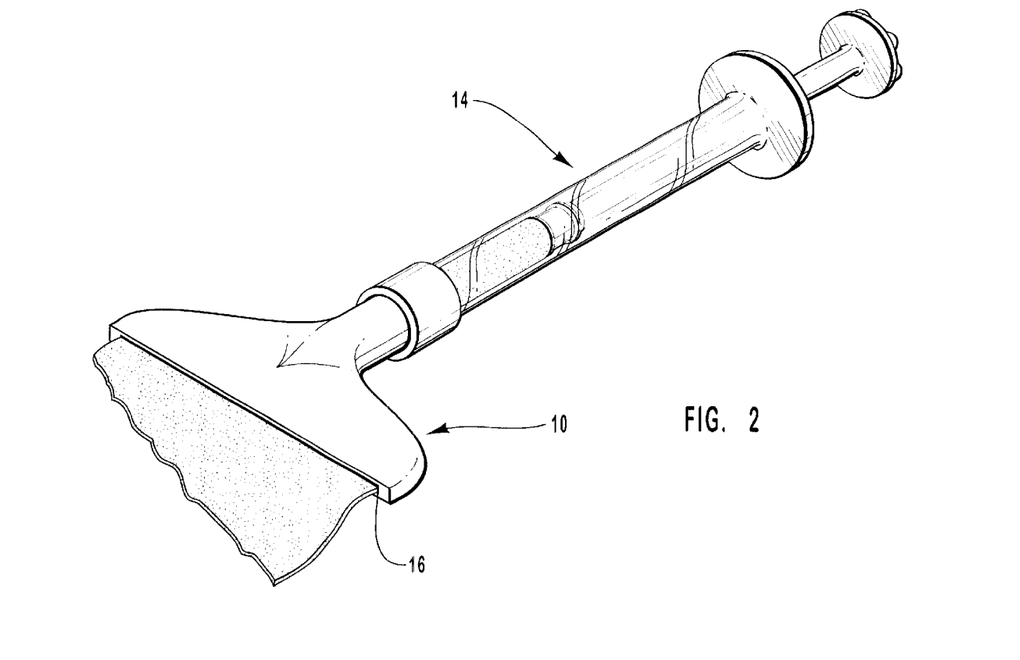
FIG. 2 shows a perspective view of a formulation storage container/delivery syringe with an applicator nozzle.

One such applicator is a delivery nozzle 10 that has one end that can be screwed onto a squeezable container 12 of the formulation, as shown in FIG. 1. Alternatively the applicator may be similar to a syringe 14 with a specialized delivery nozzle 10 as in FIG. 2. The other end of the nozzle 10 has a flat and thin opening 16 with predetermined dimensions. For example, the opening may be 10 mm long and 1 mm wide. When the formulation is squeezed out of the container 12 or forced out of the syringe 14, and through the delivery nozzle 10, it is in the shape of a 10 mm wide and 1 mm thick layer. When this layer is applied on to the skin, the thickness is relatively uniform. The nozzle 10 may be releasably or permanently attached to the container 12. FIGS. 1 and 2 show an internally threaded applicator nozzle 10 that is also compatible with a luer lock. The nozzle 10 can be screwed onto the container 12 that has a matching threaded receiving end or locked into place on syringe 14. It is also desirable to supply nozzles 10 with different widths and lengths, so that different layers of the formulation with desired thickness and width can be applied to accommodate different body surfaces and to achieve desired formulation thickness. The nozzle may also be sterile and disposable.

Figure 3:
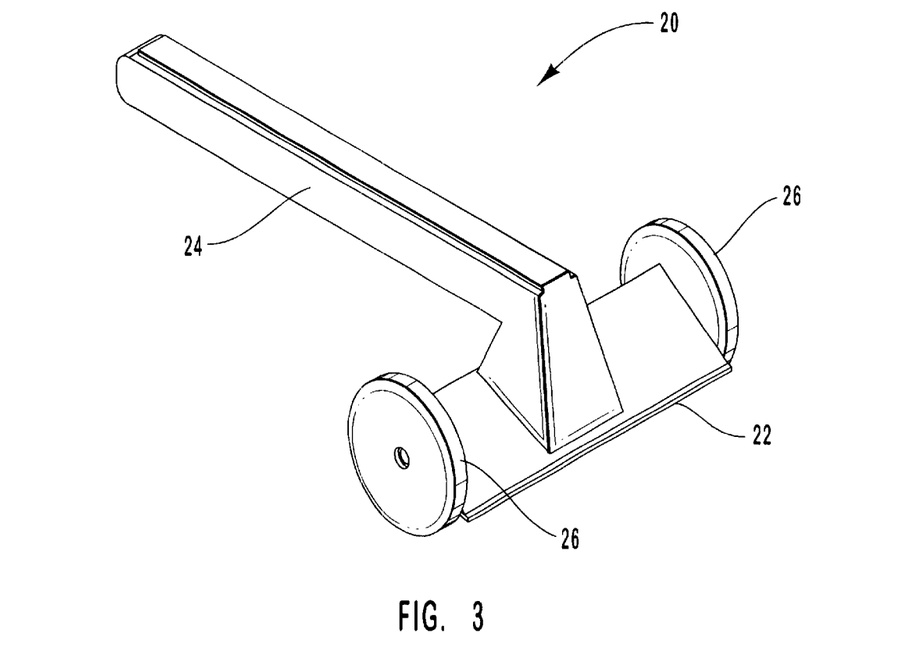
FIG. 3 shows a top view of a spatula for evenly spreading the drug formulation.
Figure 4:
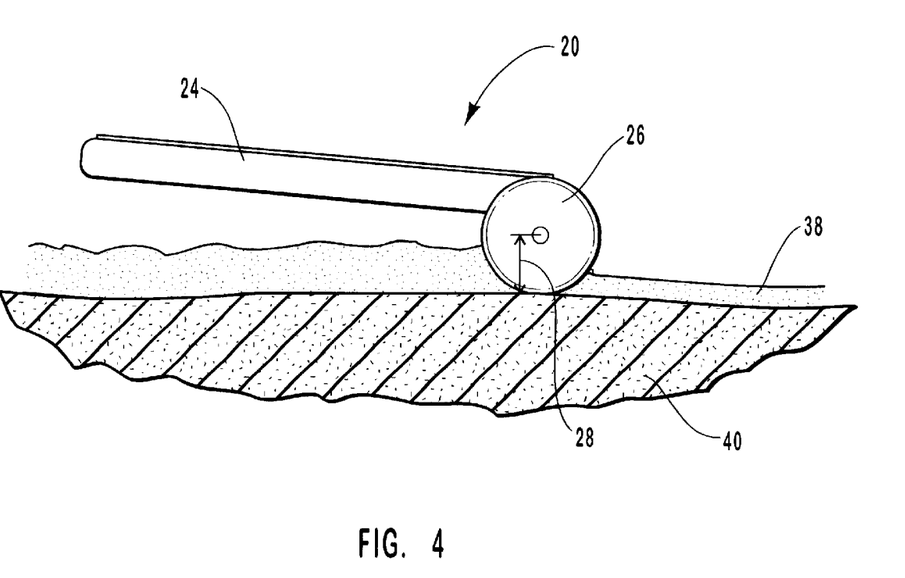
FIG. 4 shows a side view of a spatula spreading the drug formulation on a body surface.

FIGS. 3 and 4 show an apparatus for evenly spreading the formulation. The spreading spatula 20 has a blade 22 for smoothing the irregular surface of recently applied drug formulations. A handle 24 allows the blade to be easily manipulated. Spacers 26 facilitate spreading the formulation 38 with a uniform thickness, represented by line 28. The spacers 26 may be fixedly or rotatably attached to the spatula blade. After a less-than-solid drug formulation 38 has applied to a body surface 40, the spreader/spatula 20 can be brought into contact with the surface 40 and formulation 38, and drawn along the formulation to smooth the formulation and give it a uniform thickness.

Another embodiment which allows the layers of formulation to be delivered at a predetermined thickness provides a pre-formed, packaged layer of the formulation. The formulation is stored in a package container as a layer with a predetermined thickness. The storage environment and container may help to maintain the formulation layer's pre-formed shape and desired thickness. For example, the pre-formed layer may be stored in a refrigerated environment and packaged in a disposable plastic tray. Upon removal from the storage environment, the formulation layer will have a viscosity which allows the layer be molded to conform to the patient's skin while substantially retaining its pre-formed thickness. After being removed from storage and applied, the layer is still in a less-than-solid state. While the formulation is delivering drug to the skin. The formulation is also undergoing a conversion to a coherent, soft solid for a period of time. After sufficient drug is delivered, the formulation layer completes its conversion to the soft, solid face and can be peeled from the skin without leaving significant amounts of residual formulation on the skin.

The formulations and methods may also be used on human mucosal membranes. Since the onset will be much faster, the formulations need to be designed so that they solidify in a much shorter time. For example, anesthesia can be achieved using a formulation with much less or no water retaining ingredients and/or by applying a much thinner layer of the formulation on the mucosal membrane.

The self-controlling feature of the formulations provides a very important benefit. The control provided by a eutectic mixture allows for controlled release of drugs into skin that lacks a "protective barrier" to control absorption. This controlled absorption may be beneficial even in circumstances where a peelable formulation is not required. For example, when the human body surface has no stratum corneum layer, the main barrier of skin against foreign substances, the skin has no barrier to prevent rapid absorption of the dermally delivered drug, which can cause serious side effects and short duration of effect. These human body surfaces include mucosal tissues, ulcerated surfaces, traumatized skin, and post-surgical wounds. The formulation in this case does not necessarily have to be converted into a gel after application, and therefore does not require a conversion agent and many be in the form of a patch, a cream, or a paste. Therefore, it is another object of this invention to provide a another formulation in which most of the drug is disposed in the formulation as oil droplets or solid particles or dissolved in oil droplets that are emulsified in the aqueous phase of the formulation, to provide extended release of the drug into a human body surface where there is no significant barrier to absorption, such as the stratum corneum layer of the skin.

For formulations that rely on water to deliver the drugs into the skin, such as Formulation $I_A$–$I_D$, the evaporation of water will greatly reduce and substantially terminate absorption or significantly reduce the drug absorption rates. Without this feature it is possible for a user to receive dangerously high doses of the anesthetic drug being delivered. Moreover, certain skin areas are much more permeable than other skin areas. Use of the anesthetics on highly permeable skin, such as facial skin or skin lacking a protective barrier further increases the chances that prolonged exposure to the formulation will lead to dangerous toxic levels of anesthetic being delivered.

The termination or significant reduction of the drug delivery due to liquid evaporation is an important safety feature of the present invention, particularly for applications in which prolonged absorption may be harmful to the user and for applications in which the patient receiving the medication is not being closely monitored by a health care professional. For example, Formulation I is able to numb the skin in about 30–60 min. However, if the user the formulation on a larger skin area and forgets to remove the formulation after achieving the effect and leaves it on the skin for a long time, the formulation will stop delivering the drugs after water evaporates and the formulation dries. The self-terminating delivery prevents over dosing.

Transdermal drug delivery rates and doses are determined primarily by the dimensional surface area of the body surface that is in contact with the drug formulation. Drug delivery systems which do not provide the ability to control the surface area covered by the formulation make it difficult to control the, dose or rate of drug delivery. Drug delivery systems which do not allow the surface area to be varied in a regulated manner make it difficult to vary dose and rate according to varying circumstances.

The present invention provides the ability to vary and to control the surface area in contact with the formulation. By providing a formulation which converts to a solid after application as a less-than-solid formulation, the present invention allows the surface area to be varied to suit different applications, but, upon the formulation's conversion, allows the formulation to maintain the desired surface. Once solidified, the drug does not flow away from the administration to be absorbed elsewhere and thereby change the overall dose and rate of delivery. Allowing the user to chose from a variety of patches having different surface areas and fill the patches with the a drug formulation that will convert to a solid provides similar benefits.

EXAMPLE 1

A patient's facial skin must be anesthetized as part of a medical operation or procedure. A 1 mm layer of an anesthetic embodiment of Formulation I, such as Formulation $A_I$, $I_B$, or $I_C$, is applied onto the facial skip with an applicator similar to that shown in FIG. 1. After about 30 to 45 minutes, the skin is anesthetized, and the formulation becomes a layer of coherent and soft solid. The coherent and soft layer is peeled off the facial skin, and the facial skin is ready to be operated on.

EXAMPLE 2

A patient's facial skin must be anesthetized as part of a medical operation or procedure. An anesthetic embodiment of Formulation II, such as Formulation $II_A$, is applied onto the facial skin to form a 1 mm thick layer. A sheet of gauze impregnated with 1 $mg/cm^2$ sodium borate and laminated with a layer of polyurethane is placed onto the formulation layer on the facial skin, with the gauze side in direct contact with the formulation. After about 20 minutes, the formulation is converted into a solid, coherent gel by sodium borate. The skin is anesthetized at about the same time or shortly thereafter. When the laminated sheet is peeled off the skin, the gelled formulation comes off with the sheet, leaving very little residual formulation on the skin. The anesthetized facial skin is ready to be operated on.

EXAMPLE 3

A patient has a chronic ulcer in his leg that causes pain. A 1 mm layer of sterilized Formulation $I_A$ is applied onto the ulcer surface for reducing or eliminating the pain. Lidocaine and tetracaine are gradually released from the formulation to provide pain relief over an extended period of time. The formulation becomes a coherent, soft solid after 45 minutes, and is ready to be removed any time after without leaving residual formulation on the ulcer surface. In this situation, the fluid from the ulcer surface may keep the formulation moist and thus make it possible to continue delivery of the local anesthetic for an extended period of time.

EXAMPLE 4

Formulation $II_A$ is sterilized by high temperature or radiation and used to provide anesthesia for debridement for a burn patient. Formulation II is applied onto the area to be debrided to form a 1 mm thick layer. A sheet similar to that in Example 2 is placed onto the formulation layer, with the gauze side in direct contact with the formulation. After about 20 minutes, the formulation is converted into a solid, coherent gel by sodium borate. After 60 minutes, the tissue area under the formulation is significantly anesthetized, and the softened significantly by being hydrated in the formulation for 60 minutes. The laminated sheet is peeled off, and the gelled formulation comes off with the sheet, leaving very little residual formulation on the tissues. The area can now be debrided more easily and less painfully with significantly less or without systemic analgesic.

EXAMPLE 5

A modified version of Formulation $II_A$ is used to provide anesthesia for debridement of scabs. The treatment is similar to Example 4, except that the formulation in this example has no Water Lock®. The formulation in this example is the same as Formulation II, except the 1.6% Water Lock® in the formulation is replaced by water. Compared with Formulation II, this formulation is less viscous, and makes better contact with skin with scabs.

EXAMPLE 6

A formulation similar to Formulation $II_A$ is sterilized by high temperature or radiation and applied onto a post-surgical wound. The formulation does not contain the conversion agent. As discussed above, the local anesthetics are released onto the wound surface and eventually into the body in a controlled fashion and over an extended period of time to provide extended anesthetic effect and minimize the side effect potential.

EXAMPLE 7

A formulation similar to Formulation $II_A$ is applied onto an ulcerated skin or mucosal surface, or traumatized body surface. As discussed above, the local anesthetics are released onto the wound surface and eventually into the body in a controlled fashion and over an extended period of time to provide extended anesthetic effect and minimize the side effect potential.

EXAMPLE 8

Similar to Examples 6 and 7, except that the formulation does contain a conversion agent. After the application of the formulation, the patient or caregiver may selectively choose to convert the formulation to a solid gel by applying a gauze containing 1 mg/cm2 sodium borate onto the formulation to convert the formulation into a coherent and solid gel. Converting the formulation to a gel facilitates easy removal of the formulation after use.

EXAMPLE 9

Minoxidil is incorporated into a solution comprising a proper ratio of water, polyethylene glycol-600 and polyvinyl alcohol to form a viscous liquid. A layer of about 1 mm of the viscous liquid is applied onto a user's scalp before bedtime for promoting hair growth. After about 20 minutes, most of the water in the formulation is evaporated and the formulation becomes a thin, solid, and coherent film on the scalp. This minimizes the chances that the formulation is rubbed off by the pillow in the night. Substances that can increase the adhesiveness of the "dried" formulation layer to the scalp, such as certain poly acrylic adhesives, may be added into the formulation to make the "dried" formulation layer more tightly attached to the scalp.

EXAMPLE 10

A local anesthetic formulation containing thermal gel has the following components shown in Table I:

TABLE I

Anesthetic Formulation using Thermal Gel

| Ingredient | Weight Percentage |
| --- | --- |
| 1:1 (w:w) eutectic mixture of lidocaine and tetracaine | 12.0 |
| Pluronic F127 (BASF Corp.) | 25.0 |
| Lecithin | 2.3 |
| Water | 60.7 |

The components are thoroughly mixed and the eutectic mixture of lidocaine and tetracaine is in the form of small oil droplets emulsified in the aqueous phase. The formulation is a flowable liquid at room temperature. To use, the formulation is sterilized and then is applied onto a surgical wound. The temperature of the face turns the formulation into a gel which prevents the formulation from flowing away from the application site.

Active warming methods, such as infrared radiation and blowing warm air, may be used to help convert the formulation into a gel. On the other hand, a thermal gel with a conversion temperature in the range of about 28° to 33° C. may be developed and used in this formulation to substitute Pluronic F127, so that the body temperature alone is able to convert the formulation into a solidified gel.

In a preferred thermal gel embodiment, the formulation converts into a more solid state from room temperature at a temperature between 28 ° to 38° C., preferably at a temperature between 29° to 34° C. The converting of the formulation results from placing the formulation onto or into a human body having a temperature of at least 28° C.

EXAMPLE 11

A patient has a burn on the body's skin surface. The burn is treated by administering a layer of the formulation to the burned skin surface. The drug formulations deliver a medication such as an antibiotic, a local anesthetic to the burned body surface, but the formulation allows for a controlled release of the drug to the wound area. As the drug is being delivered, the formulation's phase change is initiated by applying a crosslinking agent. The crosslinking agent is sprayed onto the gel used as a mist. The droplets of the mist contain an agent capable of initiating the phase change and upon contact with the formulator are absorbed into the formulation. The mist may also provide moisture to the skin surrounding the burn areas. The formulation for treating burns is designed to allow the portion of the formulation in contact with the skin to maintain and retain some moisture, so as to facilitate hydration of burned skin areas and to allow extended delivery of the drug if desired. The solidified drug formulation provides a measure of protection for the wound surface, particularly from initiating or painful contact as well as from infection. After the formulation is substantially solidified, the solidified drug formulation can be easily removed without having to wipe off residual formulation. As an alternative to spraying a mist of crosslinking agent, gauze on fabric material soaked in a crosslinking agent can be placed over the formulation. The gauze can provide additional protection to the wound. For some treatments it may be advantageous to apply a pre-formed, moldable layer of formulation to reduce the potential for painful or infectious contact with wound.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

EXAMPLE 12

A local anesthetic embodiment formulation is incorporated into a patch and gelled with sodium borate. The formulation has the following ingredients shown in Table J:

TABLE J

Lidocaine Base Formulation using Castor oil

| Ingredients | Weight Percentage |
| --- | --- |
| lidocaine base | 5 |
| Castor oil | 15 |
| polyvinyl alcohol | 9.4 |
| lecithin | 2.4 |
| Water | 68.2 |

Oils other than castor oil, such as oleyl alcohol, may also be used for the formulation.

The patch is placed in post-surgical wound to control pain. Lidocaine dissolved in the aqueous phase permeates into the wound tissues to provide the analgesia effect, but lidocaine in the castor oil droplets can -not move directly out of the formulation because of the hindrance by the crosslinked polyvinyl alcohol network. As more dissolved lidocaine leaves the formulation, more lidocaine in the oil droplets dissolves into the aqueous phase and gets ready to permeate into the wound tissue. Since most of the lidocaine exists in the oil droplets, and the concentration of lidocaine in the aqueous phase can be reduced (by selecting the pH, i.e. 7, of the formulation), the release of lidocaine into the wound tissues is gradual and controlled. This should avoid "dumping" lidocaine into the tissue and should extend the duration of analgesic effect.

EXAMPLE 13

Similar to that in Example 1, except that the formulation is applied to the site of a mosquito bite or bee sting. The itch or the pain from the bite disappears in about one hour.

EXAMPLE 14

Similar to that in Example 1, except in this case the formulation is sterilized by high temperature or radiation, and is applied on a minor cut on skin. The pain diminishes in about 1 hour.

TABLE K

Lidocaine Base Formulation using Castor oil

| Ingredients | Weight Percentage |
| --- | --- |
| lidocaine base | 5 |
| Castor oil | 15 |
| polyvinyl alcohol | 9.4 |
| lecithin | 2.4 |
| Water | 68.2 |

EXAMPLE 15

Similar to that in Example 1, except in this case the formulation is sterilized by high temperature or radiation, and is applied on a minor cut on skin. The formulation is made of the following ingredients:

TABLE L

Lidocaine Base Formulation using Castor oil

| Ingredients | Weight Percentage |
| --- | --- |
| lidocaine base | 5 |
| Castor oil | 15 |
| polyvinyl alcohol | 9.4 |
| lecithin | 2.4 |
| WaterLock ® A-180 | 1.5 |
| Water | 66.7 |

The pain diminishes in a short period of time.

EXAMPLE 16

A patient is suffering from finale erectile dysfunction. The patent is treated using a formulation of the present invention that contains alprostadil. The formulation also employs a thermal gel. The formulation is in a liquid state during application of the formulation and is applied by inserting the formulation into the penile urethra through the opening of the urethra at the tip of the penis. Alprostadil is absorbed into the mucosal tissue. Body heat from surrounding tissues initiates the conversion of the formulation from a less-than-solid state to a "more solid" state, such as a more viscous liquid or fluid gel. Prior to conversion, the liquid formulation can flow easily into the urethra which facilitates the administration of the formulation. Following conversion of the formulation, the formulation has a more solid state which prevents the formulation from flowing out of the urethra before sufficient drug is administered, and prevents the drug from prematurely flowing away from the mucosal tissues of the urethra. After a sustainable erection is achieved, the formulation can be removed by manipulation of the urethra and surrounding tissues or by ejaculation. The formulation can be combined with other pharmaceutical agents such as contraceptives or drugs to promote conception.

EXAMPLE 17

An patient requires treatment using of a drug that is delivered transdermally. The typical transdermal dose of the drug is insufficient for the patient because the patient's body mass is large and the dimensional surface area typically used to deliver the dose is too small for the patient. Using the present invention, care giver is able to modify the does by selecting an unfilled patch having a larger treatment surface area and filling the patch with the drug formulation. The larger surface area of the patch allows the caregiver to increase the does of the drug while using the same drug formulation typically used.

What is claimed is:

1. A method of anesthetizing a human body surface comprising the steps of:
    applying a formulation to a human body surface, said formulation comprising:
        a local anesthetic;
        a conversion agent to facilitate a transformation of said formulation from an initial liquid phase to a peelable coherent, solid phase;
        a vehicle medium comprising an evaporable solvent;
    converting said formulation to said coherent, solid phase after said formulation is applied to said human body surface by evaporating said evaporable solvent from said formulation; and controlling the delivery of said local anesthetic into said human body surface by controlling the evaporation time of said evaporable solvent and conversion of said formulation into said peelable coherent, solid phase, wherein said local anesthetic is delivered into said human body surface at a determined and calculated rate sufficient to anesthetize said human body surface during evaporation of said evaporable solvent, said local anesthetic delivery continuing until and is completed upon the substantial evaporation of said evaporable solvent and conversion of said formulation into said coherent solid phase.

2. The method of claim 1, wherein said local anesthetic agent is tetracaine.

3. The method of claim 1, wherein said evaporable solvent is water.

4. The method of claim 1, wherein said human body surface is skin.

5. The method of claim 1, wherein said step of converting said formulation to a coherent, solid phase is accomplished within about 30 minutes, during which complete anesthetization of said human body surface is achieved.

6. The method of claim 1, wherein said step of converting said formulation to a coherent, solid phase is accomplished within about 60 minutes, during which complete anesthetization of said human body surface is achieved.

7. The method of claim 1, further comprising the step of peeling said formulation from said human body surface upon conversion into said coherent, solid phase.

8. The method of claim 1, wherein said conversion agent is polyvinyl alcohol.

9. The method of claim 1, wherein said conversion agent is a thermally reversible gel polymer.

10. The method of claim 9, wherein said thermally reversible gel polymer is Pluronic F127.

11. The method of claim 1, wherein said conversion agent is sodium borate.

12. The method of claim 1, wherein said conversion agent is boric acid.

13. The method of claim 1, wherein said conversion agent is a compound containing salts of boric acid.

14. The method of claim 1, wherein said conversion agent is a compound containing boron.

15. The method of claim 1, wherein said conversion agent is selected from the group of polyvinyl alcohol and carrageenan.

16. The method of claim 1, wherein said conversion agent is selected from the group of: polyvinyl alcohol, carrageenan, gellan gum, polyvinyl pyrrolidone, sodium carboxymethyl cellulose, hydroxyethyl cellulose, bydroxypropyl cellulose and other cellulose derivatives.

17. The method of claim 1, wherein said conversion agent is a polymer.

18. The method of claim 1, wherein said conversion agent is a compound selected from boric acid and sodium borate.

19. The method of claim 1, wherein said conversion agent is selected from the group of boric acid and salts of boric acid.

20. The method of claim 1, wherein said conversion agent is boron.

21. The method of claim 1, wherein said conversion agent is a compound comprising calcium.

22. The method of claim 1, wherein said conversion agent is a thermal gel capable of becoming more solid at a temperature between 20° C. to 37° C.

23. The method of claim 1, wherein said conversion agent is chosen from the group of sodium borate, salts of boric acid and boric acid.

24. The method of claim 1, wherein said transformation is passively triggered.

25. The method of claim 24, wherein said transformation is passively triggered by a change in environment.

26. The method of claim 24, wherein said transformation is passively triggered by a change in the water content of said formulation.

27. The method of claim 24, wherein said transformation is passively triggered by exposing the formulation to human body surface temperature.

28. The method of claim 24, wherein said transformation is passively triggered by exposing the formulation to air.

29. The method of claim 24, wherein said transformation is passively triggered by exposing the formulation to light.

30. The method of claim 24, wherein said transformation is passively triggered by removing the formulation from a storage environment to allow conversion to take place.

31. The method of claim 24, wherein said transformation is passively triggered by exposing the formulation to ambient environmental conditions.

32. The method of claim 31, wherein said ambient environmental conditions are exposure to various wavelengths of electromagnetic radiation, to temperatures, to humidity levels, or to atmospheric gases.

33. The method of claim 1, wherein said transformation is actively triggered.

34. The method of claim 33, wherein said transformation is actively triggered by changing the ambient environment.

35. The method of claim 33, wherein said transformation is actively triggered by changing the chemical makeup of the formulation.

36. The method of claim 33, wherein said transformation is actively triggered by exposing the formulation to a high level of light.

37. The method of claim 33, wherein said transformation is actively triggered by adding a pharmaceutical ingredient to the formulation.

38. The method of claim 33, wherein said transformation is actively triggered by crosslinking a crosslink agent.

39. The method of claim 38, wherein said crosslinking agent comprises covering said formulation with a sheet of material impregnated with said crosslinking agent.

40. The method of claim 33, wherein said transformation is actively triggered by controlling water loss the formulation.

41. The method of claim 33, wherein said transformation is actively triggered by crosslinking a polymer in said formulation using ultraviolet radiation.

42. The method of claim 1, wherein said transformation comprises placing a layer of said formulation onto a human body surface having a temperature of at least 28° C.

43. The method of claim 1, wherein said transformation is triggered by heating.

44. The method of claim 1, wherein said transformation is triggered by blowing heated air onto said formulation on said human body surface.

45. The method of claim 1, wherein said transformation is triggered by radiating infrared radiation onto said formulation on said human body surface.

46. The method of 1, wherein said transformation is triggered by placing a patch capable of generating heat onto said formulation on said human body surface.

47. The method of 46, the heat of said patch is generated by an exothermic reaction.

48. A method of 1, wherein said transformation significantly reduces the rate of drug delivery.

49. A method of 1, wherein said transformation substantially terminates drug delivery upon completion of said conversion.

50. A method of 1, wherein said transformation prevents over dosing.

51. A method of anesthetizing a human body surface comprising the steps of:
- applying a formulation to a human body surface, said formulation comprising:
  - a local anesthetic;
  - a conversion agent to facilitate a transformation of said formulation from an initial liquid phase to a peelable coherent, solid phase;
  - a vehicle medium comprising an evaporable solvent;
- converting said formulation to said coherent, solid phase after said formulation is applied to said human body surface by evaporating said evaporable solvent from said formulation; and
- delivering of said local anesthetic into said human body surface at sufficient rates that the anesthetizing of said human body surface is achieved during the evaporation of said evaporable solvent; said evaporable solvent and said formulation having such a property that the complete evaporation of said evaporable solvent from said formulation substantially stops the delivery of said local anesthetic into said human body surface.

52. The method of claim 51, wherein said local anesthetic agent is lidocaine.

53. The method of claim 51, wherein said local anesthetic agent is tetracaine.

54. The method of claim 51, where said evaporable solvent is water.

55. The method of claim 51, wherein said human body surface is skin.

56. The method of claim 51, where said step of converting said formulation to a coherent, solid phase is accomplished within about 30 minutes, during which complete anesthetization of said human body surface is achieved.

57. The method of claim 51, wherein said step of converting said formulation to a coherent, solid phase is accomplished within about 60 minutes, during which complete anesthetization of said human body surface is achieved.

58. The method of claim 51, further comprising the step of peeling said formulation from said human body surface upon conversion into said coherent solid phase.

59. The method of claim 51, wherein said conversion agent is polyvinyl alcohol.

60. The method of claim 51, wherein said conversion agent is a thermally reversible gel polymer.

61. The method of claim 51, wherein said thermally reversible gel polymer is Pluronic F127.

62. The method of claim 51, wherein said conversion agent is selected from the group of polyvinyl alcohol and carrageenan.

63. The method of claim 51, wherein said conversion agent is selected from the group of: polyvinyl alcohol, carrageenan, gellan gum, polyvinyl pyrrolidone, sodium carboxymethyl cellujose, hydroxyethyl cellulose, hydroxypropyl cellulose and other cellulose derivatives.

64. The method of claim 51, wherein said conversion agent is a polymer.

65. The method of claim 51, wherein said conversion agent is a thermal gel capable of becoming more solid at a temperature between 20° C. to 37° C.

66. A method of anesthetizing a human body surface comprising applying a formulation to a human body surface, said formulation comprising:
- a local anesthetic;
- a conversion agent to facilitate a transformation of said formulation from an initial liquid phase to a peelable coherent, solid phase; and
- a vehicle medium comprising an evaporable solvent; said formulation converting to said coherent, solid phase after said formulation is applied to said human body surface by evaporation of said evaporable solvent from said formulation; said formulation delivering said local anesthetic into said human body surface during the evaporation of said evaporable solvent and having sufficient delivery rate of said local anesthetic into said human body surface such that the anesthetizing of said human body surface is achieved during the evaporation of said evaporable solvent.

67. The method of claim 66, wherein said conversion agent is polyvinyl alcohol.

68. The method of claim 66, wherein said conversion agent is a polymer.

69. The method of claim 66, wherein said evaporation of said evaporable solvent is facilitated by heat.

70. The method of claim 66, wherein said local anesthetic is tetracaine.

71. The method of claim 66, wherein said local anesthetic is lidocaine.

72. A method of anesthetizing a human body surface comprising the steps of applying a formulation to a human body surface, said formulation comprising:
- a local anesthetic;
- a conversion agent to facilitate a transformation of said formulation from an initial liquid phase to a peelable coherent, solid phase;
- a vehicle medium comprising an evaporable solvent;
- converting said formulation to said coherent, solid phase after said formulation is applied to said human body surface by the evaporation of said evaporable solvent from said formulation; and
- delivering said local anesthetic into said human body surface at sufficient rates such that the anesthetizing of said human body surface is achieved during the evaporation of said evaporable solvent.

73. The method of claim 72, wherein said converting said formulation to said coherent, solid phase comprises applying said formulation to said human body surface and exposing said formulation to air.

74. The method of claim 72, wherein said delivering of said local anesthetic into said human body surface comprises placing said formulation into contact with said human body surface.

75. A method of anesthetizing a human body surface comprising applying a formulation to a human body surface, said formulation comprising:
- a local anesthetic;
- a conversion agent to facilitate a transformation of said formulation from an initial liquid phase to a peelable coherent, solid phase;
- a vehicle medium comprising an evaporable solvent; said formulation converting to said coherent, solid phase after said formulation is applied to said human body surface by evaporating said evaporable solvent from said formulation; and said formulation delivering said local anesthetic into said human body surface at sufficient rates that the anesthetizing of said human body surface is achieved during the evaporation of said evaporable solvent and is substantially completed upon the conversion of said formulation into said coherent, solid phase.

76. A paste formulation for delivering local anesthetic into a human body surface comprising:

a local anesthetic;

a conversion agent to facilitate the transformation of said formulation from an initial paste phase to a peelable coherent, solid phase; and an evaporable solvent; the presence of said solvent being necessary in order for said formulation to deliver said local anesthetic into normal human skin at sufficient rates capable of anesthetizing a normal human within sixty minutes.

77. The formulation of claim 76, wherein the local anesthetic agent is lidocaine.

78. The formulation of claim 76, wherein the local anesthetic agent is tetracaine.

79. A method of anesthetizing a human body surface comprising the steps of:

applying a formulation to a human body surface, said formulation comprising:

a local anesthetic;

a conversion agent to facilitate the transformation of said formulation from an initial liquid phase to a peelable coherent, solid phase;

a vehicle medium comprising an evaporable solvent;

converting said formulation to said coherent, solid phase after said formulation is applied to said human body surface by evaporating said evaporable solvent from said formulation; and delivering said local anesthetic into said human body surfaced at such rates so that the anesthetizing of said human body surface and conversion of said formulation into said solid phase take place within a short time from each other; said solvent having a property that the complete evaporation of it from the formulation substantially stops the delivering of said local anesthetic into said human body surface.

80. A method of anesthetizing a human body surface comprising the steps of:

applying a formulation to a human body surface, said formulation comprising:

a local anesthetic;

a conversion agent to facilitate the transformation of said formulation from an initial liquid phase to a peelable coherent, solid phase;

a vehicle medium comprising and evaporable solvent;

converting said formulation to said coherent, solid phase after said formulation is applied to said human body surface by evaporating said evaporable solvent from said formulation; and delivery of said local anesthetic into said human body surface by evaporating said evaporable solvent and conversing of said formulation into said peelable coherent, solid phase, wherein said local anesthetic is delivered into said human body surface in the liquid phase sufficient to anesthetize said human body surface during evaporation of said evaporable solvent, said local anesthetic delivery continuing until substantial evaporation of said evaporable solvent.

81. The method of claim 72, wherein said conversion agent is polyvinyl alcohol.

82. The method of claim 75, wherein said conversion agent is polyvinyl alcohol.

83. The method of claim 76, wherein said conversion agent is polyvinyl alcohol.

84. The method of claim 79, wherein said conversion agent is polyvinyl alcohol.

85. The method of claim 80, wherein said conversion agent is polyvinyl alcohol.

* * * * *